United States Patent [19]

Bayham et al.

[11] 4,181,140

[45] Jan. 1, 1980

[54] FRANGIBLE RESEALABLE CLOSURE FOR A FLEXIBLE TUBE HAVING HOLD OPEN MEANS

[75] Inventors: Edward L. Bayham; Ronald A. Williams, both of Mundelein; David W. Ammann, Lindenhurst, all of Ill.

[73] Assignee: Baxter Travenol Laboratories, Inc., Deerfield, Ill.

[21] Appl. No.: 876,790

[22] Filed: Feb. 10, 1978

[51] Int. Cl.$^2$ .............................................. A61M 5/14
[52] U.S. Cl. ................. 137/68 R; 128/214.2; 251/342
[58] Field of Search ............. 137/68 R, 797; 251/342; 128/214 D, 214.2

[56] References Cited

U.S. PATENT DOCUMENTS

| 3,158,165 | 11/1964 | Benson et al. | 137/68 R |
| 3,470,893 | 10/1969 | Nelson | 137/797 X |
| 3,685,795 | 8/1972 | Caster | 251/342 |
| 4,055,179 | 10/1977 | Manshot et al. | 128/274 X |
| 4,080,965 | 3/1978 | Phillips | 128/214 D |

FOREIGN PATENT DOCUMENTS 402286  11/1965  Switzerland .................. 128/214 D

*Primary Examiner*—Martin P. Schwadron
*Assistant Examiner*—Richard Gerard
*Attorney, Agent, or Firm*—Paul C. Flattery; H. W. Collins; Garrettson Ellis

[57] ABSTRACT

Valve means in a flexible tube, for example, tubing for connecting blood bags, are provided, which comprises a tubular portion having a closed end, and an elongated, generally rigid member, carried on the exterior of the closed end and positioned within the flexible tube. Frangible means are provided to permit the opening of the closed end by manual manipulation of the elongated member from outside of the flexible tube. The elongated, rigid member is adapted to fit in sealing relationship within the tubular portion after opening of the closed end, to permit resealing of the valve. The elongated, generally rigid member carries longitudinal vanes to provide flow channels along its length. In accordance with this invention, a pair of said vanes in opposed relationship extends rearwardly of the end of the central portion of the rigid member, and the flexible tube defines a bore portion position to receive and resiliently hold the proposed veins when the frangible means is broken and the rigid member is separated from the tubular portion. This prevents accidental reclosing of the valve means by the rigid member moving to obstruct the tubular portion.

9 Claims, 3 Drawing Figures

FRANGIBLE RESEALABLE CLOSURE FOR A FLEXIBLE TUBE HAVING HOLD OPEN MEANS

BACKGROUND OF THE INVENTION

In U.S. Pat. application, Ser. No. 818,357, filed July 25, 1977, by Garry L. Carter, Daniel B, Granzow and Edward L. Bayham, and assigned to Baxter Travenol Laboratories, Inc., a valve-type seal for a flexible tube is provided for connection between blood bags or any other desired use. The valve comprises a tubular portion having a closed end, and an elongated, generally rigid member carried on the exterior of the closed end, and positioned within the flexible tube. Frangible means are provided to permit the opening of the closed end by manual manipulation of the elongated member from outside of the flexible tube by bending the elongated member. This frangible means may optionally be an annular line of tearing weakness, or may simply result from the geometry of the structure without need for a specially-formed line of tearing weakness.

The structure of the previously cited application thus may be opened from the exterior, and may also be reclosed by reinsertion of the elongated, generally rigid member back into the tubular portion for sealing purposes.

In accordance with this present invention, a capability is provided to the above type valve to permit a valve structure to be openable by separation of the elongated, generally rigid member from the end of the tubular portion, while providing means for positively retaining and holding the elongated, generally rigid member in its open, flow-permitting position, so that an accidental reclosing of the valve by the elongated member falling back into obstructing relationship will not take place. This provides a valve that can reliably remain in the open position under flow from either direction.

DESCRIPTION OF THE INVENTION

In accordance with this invention, valve means are provided for a flexible tube, which comprises: a tubular portion having a closed end, an elongated, generally rigid member carried on the exterior of said closed end and positioned within the flexible tube, and frangible means to permit the opening of said closed end by rupture of an area of weakness defined in said closed end by manual manipulation of said elongated member from outside of the flexible tube.

In this invention, the elongated, generally rigid member defines longitudinal vanes to provide flow channels along its length, so that the member does not obstruct flow within the tube.

Preferably, the vanes may be of unequal length, with a pair of opposed vanes extending rearwardly of the end of the central portion of the rigid member. The flexible tube surrounding the rigid member may then define a preferably conical portion, positioned to receive and resiliently hold the opposed, longer vanes after the frangible means have been broken and the rigid member separated from the tubular portion. This can hold the valve in open position to prevent its accidental reclosing by the rigid member moving to obstruct the tubular portion.

Figure 1:
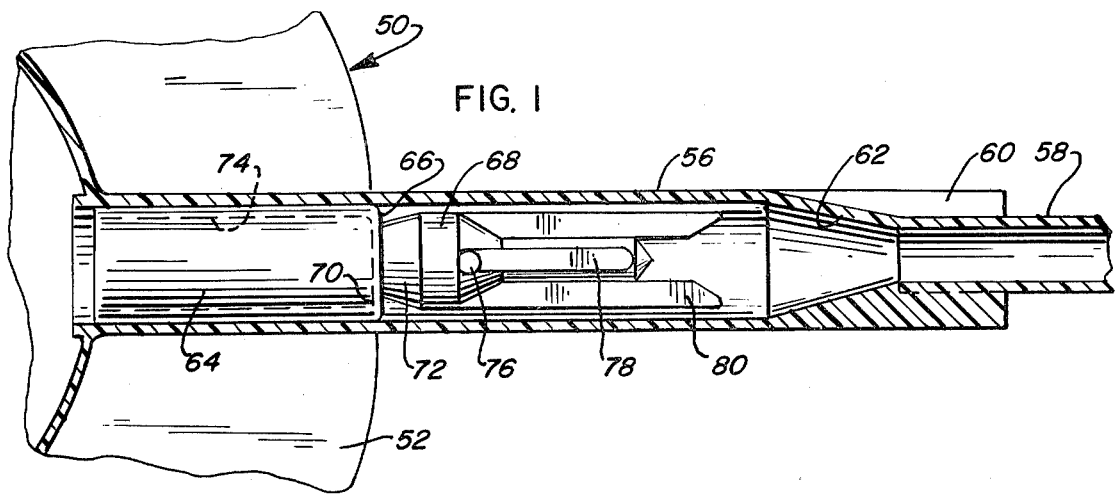
FIG. 1 is a greatly enlarged view of one embodiment of the valve of this invention, in conjunction with a blood bag, and a blood transfer tube leading to a second blood bag, with some of the parts shown in longitudinal section.
Figure 2:
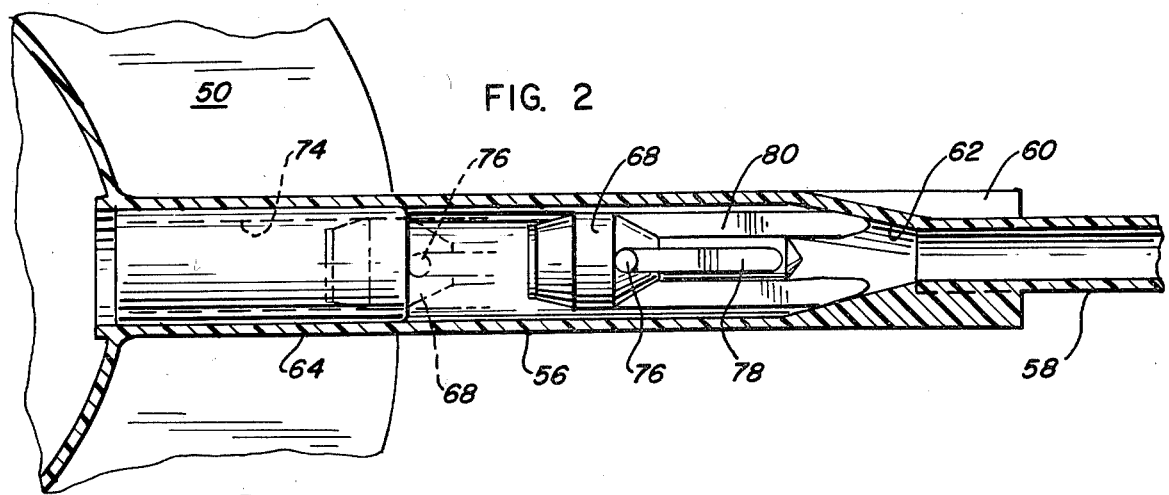
FIG. 2 is a view similar to FIG. 1 showing the valve under the condition where the elongated, rigid member is being retained in its open position.
Figure 3:
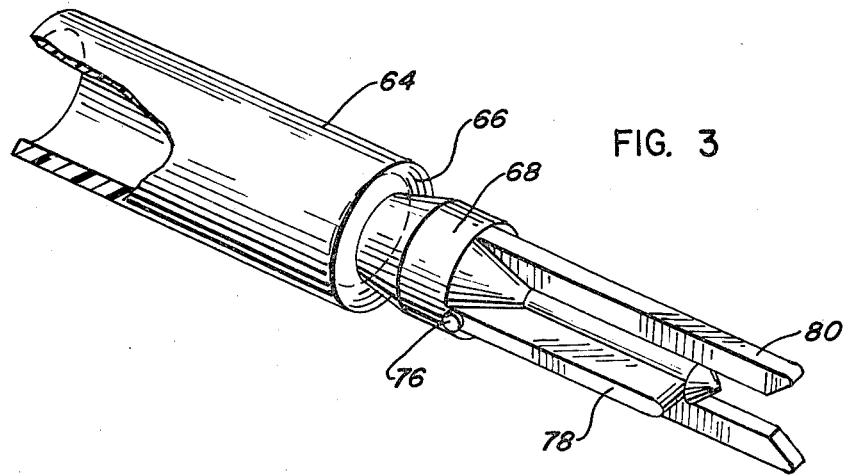
FIG. 3 is a perspective view, with portions broken away, of the tubular portion and elongated, rigid member of this invention.

Referring to FIGS. 1 through 3, the valve of this invention is shown, by way of example, to be in conjunction with blood bag 50, which, in turn, defines a flat seal 52 which surrounds and holds flexible flow tubing 56 in sealingly communicating relationship with the interior of bag 50. Tubing 56 is of relatively enlarged diameter, when compared with flow tubing 58, the two sections of tubing being conventionally joined together by a crimped or "fourway" heat seal 60 of the general type as shown in U.S. Pat. No. 2,702,036. Flow tubing 58 may communicate with another blood bag, if desired to provide a conventional "multiple bag" system utilizing the improved valve of this invention. Alternatively, the valve of this invention may be used in any desired apparatus for controlling fluid flow.

Preferably, the junction between tubes 56 and 58 defines a bore 62 of conical shape as shown.

Secured within the proximal end of tubing 56 is a preferably generally rigid tubular portion 64, having a closed end 66. Closed end 66 carries an elongated, generally rigid member 68 in integral relation thereto, for the purpose of permitting the tearing open of the end of tubular portion 64 for opening of the valve, as described above.

In the specific embodiment shown, no line of weakness is specifically formed in the junction between tubular portion 64 and elongated member 68, but a tearing action can take place by bending of elongated member 68. The relatively thin area 70 between the inner wall of tubular portion 64 and the solid mass of elongated member 68 is accordingly stressed so that area 70, which is an annular area about member 68, is ruptured by manipulation of elongated member 68 from the exterior of tube 56, and thus constitutes the line of weakness without a special groove.

Elongated, generally rigid member 68 includes a tapered portion 72 for fitting within the bore 74 of tubular portion 64 after opening for reclosing the structure again, as shown in phantom in FIG. 2.

Studs 76 are provided to project outwardly to prevent the excess insertion of elongated member 68 into bore 74, which could render the removal of member 68 difficult at a later time. Studs 76 bear against the end of tubular portion 64 when member 68 is inserted to the proper depth, preventing further insertion.

As in the previous embodiments, elongated, generally rigid member 68 defines a plurality of longitudinal vanes 78, 80. However, vanes 80 are of unequal length to vanes 78, being longer and preferably sufficiently long to exhibit a perceptible spring-like resilience.

Accordingly, upon manual opening of the valve by bending of generally rigid member 68 to rip open weakened area 70, member 68 may be manually moved backwards, by axially collapsing, gripping, and re-extending flexible tube 56, to be placed into pinching, resilient, retention relation between vanes 80 and conical bore portion 62, as shown in FIG. 2. Accordingly, rigid member 68 may be retained there, with the flow of blood or other fluid passing longitudinally around the member 68 between the respective vanes 78, 80. This permits bidirectional flow of fluid as desired through the valve without the danger of rigid member 68 drifting into obstructing relationship with bore 74 of tubular portion 64 until by positive manual action the rigid member 68 is released from its retained relation with bore 62.

Accordingly, as desired, the valve of this invention may be positively opened and retained open, as shown in FIG. 2, and may be positively resealed, after opening, by manipulation from outside the exterior of flexible tubing 56, after initial opening.

For the most convenient manipulation, flexible tubing 56 is fabricated to be quite soft so that it may be axially collapsed during manipulation of generally rigid member 68, with the tubing 56 convoluting outwardly as necessary during the process. Accordingly, rigid member can be grasped and moved because of the flexibility of tubing 56.

Also, if desired, because of the flexibility of tube 56, an outside clamp may be used to retain rigid member 68 in any desired open or closed position.

As a further modification, reduced diameter tube 58 may be enlarged somewhat and the tapered portion 62 eliminated, so that vanes 80 can project directly into the reduced diameter tubing 58, flexing inwardly somewhat as they do, for an equivalent type of retention in the open position.

The above is for illustrative purposes only, and is not intended to limit the scope of the invention of this application, which is as defined in the claims below.

That which is claimed is:

1. In a flexible tube, valve means positioned in said tube, said valve means comprising: a tubular portion having a closed end, an elongated, generally rigid member carried on the exterior of said closed end and positioned within said flexible tube, and frangible means to permit the opening of said tubular portion adjacent said closed end by rupture of an area of weakness by manual manipulation of the elongated member from outside of the flexible tube, causing separation of the elongated member from said tubular portion, said elongated, generally rigid member generally defining longitudinal vanes to provide flow channels along its length, the improvement comprising, in combination: at least some of its vanes extending rearwardly of the end of the central portion of said rigid member, said flexible tube defining a bore portion positioned to receive and resiliently hold said extending vanes without closing said flow channels when the frangible means is broken and said rigid member is separated from the tubular portion, to prevent accidental reclosing of the said tubular portion opening by the rigid member moving to obstruct said tubular portion.

2. The valve means of claim 1 in which said vanes are of unequal length, a pair of opposed vanes of equal length extending rearwardly of the end of the central portion to be received by the bore portion of the flexible tube.

3. The valve means of claim 2 in which said bore portion is conical in shape for receiving said vanes.

4. The valve means of claim 2 in which said elongated, generally rigid member includes a tapered portion for fitting within the bore of the tubular portion after opening, for reclosing the valve again.

5. The valve means of claim 4 in which stud means are provided to said elongated, generally rigid member to limit the extent of insertion of said rigid member into the tubular portion.

6. In a flexible tube, valve means positioned in said tube, said valve means comprising a tubular portion having a closed end, an elongated, generally rigid member carried on the exterior of said closed end and positioned within said flexible tube, and frangible means to permit the opening of said tubular portion by rupture of an area of weakness by manual manipulation of the elongated member from outside of the flexible tube causing separation of the elongated member from said tubular portion, said elongated, generally rigid member defining longitudinal vanes to provide flow channels along its length, the improvement comprising, in combination, at least some of its vanes extending rearwardly at the end of the central portion of said rigid member, said flexible tube defining a bore portion positioned to receive and resiliently hold said extending vanes without closing said flow channels when the frangible means is broken, to prevent accidental reclosing of said valve means by the rigid member moving to obstruct said tubular portion.

7. The valve means of claim 6 in which said vanes are of unequal length, a pair of opposed vanes of equal length extending rearwardly of the end of the central portion to be received by the bore portion of the flexible tube.

8. The valve means of claim 7 in which said bore portion is conical in shape for receiving said vanes.

9. The valve means of claim 8 in which stud means are provided to said elongated, generally rigid member to limit the extent of insertion of said rigid member into the tubular portion.

* * * * *